(12) United States Patent
Rauhala et al.

(10) Patent No.: US 11,270,598 B2
(45) Date of Patent: Mar. 8, 2022

(54) PHYSICAL ACTIVITY COACHING PLATFORM WITH DYNAMICALLY CHANGING WORKOUT CONTENT

(71) Applicant: PEAR Sports LLC, Solana Beach, CA (US)

(72) Inventors: Kari Kristian Rauhala, Solana Beach, CA (US); Simon Sollberger, San Francisco, CA (US); Joseph Rzepiejewski, Dana Point, CA (US); Eric Franchomme, San Diego, CA (US); Robert G. Allison, Corona Del Mar, CA (US)

(73) Assignee: Pear Sports LLC, Solana Beach, CA (US)

( * ) Notice: Subject to any disclaimer, the term of this patent is extended or adjusted under 35 U.S.C. 154(b) by 0 days.

(21) Appl. No.: 16/865,681

(22) Filed: May 4, 2020

(65) Prior Publication Data

US 2020/0265734 A1    Aug. 20, 2020

Related U.S. Application Data

(63) Continuation of application No. 15/017,537, filed on Feb. 5, 2016, now Pat. No. 10,643,483, which is a (Continued)

(51) Int. Cl.
*G09B 5/00* (2006.01)
*G09B 5/04* (2006.01)
(Continued)

(52) U.S. Cl.
CPC ........... *G09B 5/04* (2013.01); *G06Q 10/0639* (2013.01); *G06Q 30/0251* (2013.01);
(Continued)

(58) Field of Classification Search
CPC .............. G09B 19/003; G09B 19/0038; A61B 2230/062; A63B 24/0075; A63B 2230/062
See application file for complete search history.

(56) References Cited

U.S. PATENT DOCUMENTS 5,673,691 A    10/1997  Abrams et al.
5,857,939 A     1/1999  Kaufman
(Continued)

FOREIGN PATENT DOCUMENTS

CN    101619986    1/2010
GB      2293896    4/1996
(Continued)

OTHER PUBLICATIONS

Barbeau et al. "The Travel Assistant Device: Utilizing GPS-Enabled Mobile Phones to Aid Transit Riders With Special Needs." Presented at the 15th World Congress on Intelligent Transportation Systems. New York. Paper No. 30429. (Nov. 16-18, 2008):1-12.
(Continued)

*Primary Examiner* — Peter R Egloff
(74) *Attorney, Agent, or Firm* — Lowenstein Sandler LLP

(57) ABSTRACT

A computer implemented coaching platform is described that utilizes contextual data associated with a user and/or his environment in order to provide dynamically changing content while the user is undergoing physical activity. Related apparatus, systems, techniques and articles are also described.

20 Claims, 5 Drawing Sheets

Related U.S. Application Data continuation of application No. 14/251,457, filed on Apr. 11, 2014, now abandoned.

(60) Provisional application No. 61/856,500, filed on Jul. 19, 2013.

(51) Int. Cl.

| | |
|---|---|
| *G06Q 10/06* | (2012.01) |
| *G06Q 30/02* | (2012.01) |
| *G16H 20/40* | (2018.01) |
| *G16H 20/30* | (2018.01) |
| *A61B 5/024* | (2006.01) |
| *A61B 5/00* | (2006.01) |
| *A63B 24/00* | (2006.01) |
| *G09B 19/00* | (2006.01) |

(52) U.S. Cl.
CPC ......... *G06Q 30/0269* (2013.01); *G16H 20/30* (2018.01); *G16H 20/40* (2018.01); *A61B 5/024* (2013.01); *A61B 5/742* (2013.01); *A63B 24/0075* (2013.01); *G09B 19/003* (2013.01)

(56) References Cited

U.S. PATENT DOCUMENTS

| | | |
|---|---|---|
| 5,890,997 A | 4/1999 | Roth |
| 5,921,891 A | 7/1999 | Browne |
| 5,976,083 A | 11/1999 | Richardson et al. |
| 6,249,542 B1 | 6/2001 | Kohli et al. |
| 6,251,048 B1 | 6/2001 | Kaufman |
| 6,458,060 B1 * | 10/2002 | Watterson .......... A63B 22/0235 482/54 |
| 6,582,342 B2 | 6/2003 | Kaufman |
| 6,672,991 B2 | 1/2004 | OMalley |
| 6,702,719 B1 | 3/2004 | Brown et al. |
| 6,997,852 B2 | 2/2006 | Watterson et al. |
| 7,003,122 B2 | 2/2006 | Chen |
| 7,062,225 B2 | 6/2006 | White |
| 7,097,588 B2 * | 8/2006 | Watterson ............ A61B 5/0245 482/1 |
| 7,175,601 B2 | 2/2007 | Verjus et al. |
| 7,251,454 B2 | 7/2007 | White |
| 7,278,966 B2 | 10/2007 | Hjelt et al. |
| 7,308,360 B2 | 12/2007 | Bou-Ghannam et al. |
| 7,409,288 B1 | 8/2008 | Krull et al. |
| 7,455,622 B2 | 11/2008 | Watterson et al. |
| 7,519,327 B2 | 4/2009 | White |
| 7,658,695 B1 | 2/2010 | Amsbury et al. |
| 7,702,457 B2 | 4/2010 | Matsunaga et al. |
| 7,741,975 B2 | 6/2010 | Shum et al. |
| 7,789,800 B1 | 9/2010 | Watterson et al. |
| 7,805,149 B2 | 9/2010 | Werner et al. |
| 7,811,201 B1 | 10/2010 | Mikan et al. |
| 7,841,967 B1 | 11/2010 | Kahn et al. |
| 7,909,737 B2 | 3/2011 | Ellis et al. |
| 7,931,563 B2 | 4/2011 | Shaw et al. |
| 7,962,284 B2 | 6/2011 | Cutitta, II |
| 8,033,959 B2 | 10/2011 | Oleson et al. |
| 8,386,166 B2 | 2/2013 | Jones et al. |
| 8,506,457 B2 | 8/2013 | Baudhuin |
| 9,886,871 B1 | 2/2018 | Rauhala et al. |
| 2003/0088196 A1 | 5/2003 | Steve |
| 2003/0171189 A1 | 9/2003 | Kaufman |
| 2003/0224337 A1 | 12/2003 | Shum et al. |
| 2004/0102931 A1 | 5/2004 | Ellis |
| 2004/0153007 A1 | 8/2004 | Harris et al. |
| 2005/0107216 A1 | 5/2005 | Lee et al. |
| 2005/0192025 A1 | 9/2005 | Kaplan |
| 2005/0202934 A1 | 9/2005 | Olrik et al. |
| 2005/0209050 A1 | 9/2005 | Bartels |
| 2006/0074555 A1 | 4/2006 | Liu et al. |
| 2007/0135264 A1 | 6/2007 | Rosenberg |
| 2007/0150192 A1 | 6/2007 | Wakamatsu et al. |
| 2008/0005276 A1 | 1/2008 | Frederick |
| 2008/0108481 A1 | 5/2008 | Limma et al. |
| 2008/0109158 A1 | 5/2008 | Huhtala et al. |
| 2008/0183385 A1 | 7/2008 | Horn |
| 2008/0305933 A1 | 12/2008 | Chang |
| 2009/0004764 A1 | 1/2009 | Ohnuma et al. |
| 2009/0069156 A1 | 3/2009 | Kurunmaki et al. |
| 2009/0075781 A1 | 3/2009 | Schwarzberg et al. |
| 2010/0048358 A1 | 2/2010 | Tchao et al. |
| 2010/0056341 A1 | 3/2010 | Ellis et al. |
| 2010/0095209 A1 | 4/2010 | Gupta et al. |
| 2010/0190609 A1 | 7/2010 | Shum et al. |
| 2010/0197463 A1 | 8/2010 | Haughay, Jr. et al. |
| 2010/0216601 A1 | 8/2010 | Saalasti et al. |
| 2010/0248901 A1 | 9/2010 | Martens |
| 2010/0292050 A1 | 11/2010 | DiBenedetto et al. |
| 2010/0331147 A1 | 12/2010 | Mikan et al. |
| 2011/0071003 A1 | 3/2011 | Watterson et al. |
| 2011/0092337 A1 | 4/2011 | Srinivasan et al. |
| 2011/0105279 A1 | 5/2011 | Herranen |
| 2011/0152696 A1 * | 6/2011 | Ryan ................. G09B 19/0038 600/481 |
| 2011/0153194 A1 | 6/2011 | Bellerose |
| 2011/0273552 A1 | 11/2011 | Wang et al. |
| 2012/0109657 A1 | 5/2012 | Partan |
| 2012/0253663 A1 | 10/2012 | Hani et al. |
| 2012/0271143 A1 | 10/2012 | Aragones et al. |
| 2013/0040271 A1 | 2/2013 | Rytky et al. |
| 2013/0173155 A1 | 7/2013 | Fino |
| 2013/0196821 A1 * | 8/2013 | Watterson .............. G16H 20/30 482/9 |
| 2013/0345975 A1 | 12/2013 | Vulcano et al. |
| 2014/0135960 A1 | 5/2014 | Choi |
| 2014/0272855 A1 | 9/2014 | Maser et al. |
| 2015/0081062 A1 | 3/2015 | Fyfe et al. |
| 2015/0081210 A1 | 3/2015 | Yeh et al. |
| 2015/0118657 A1 | 4/2015 | Shrake et al. |
| 2016/0163224 A1 | 6/2016 | Rauhala et al. |
| 2016/0240100 A1 | 8/2016 | Rauhala et al. |

FOREIGN PATENT DOCUMENTS

| | | |
|---|---|---|
| GB | 2454705 | 5/2009 |
| KR | 20120010848 | 2/2012 |
| WO | 9402904 | 2/1994 |
| WO | 9949279 | 9/1999 |
| WO | 2009003890 | 1/2009 |

OTHER PUBLICATIONS

Holland et al. "AudioGPS: spatial audio in a minimal attention interface." Personal and Ubiauitous Computina. 6(4):(2002); 14 paGes.

Schoning et al. "WikEar—Automatically Generated Location-Based Audio Series between Public City Maps," In adjunct Proc. of Ubicomp '07. (2007). 4 pages.

"Single Language GPS Commentary Systems." AudioConexus. Web. Jul. 9, 2013. 3 pages.

* cited by examiner

FIG. 3

| MM:SS | Type | Option | Comment | Audio |
|---|---|---|---|---|
| 00:00 | Zone | 1 | Start of Workout, ease into it | 🔊 |
| 02:00 | Prompt | | Settle in and focus on tech | 🔊 |
| 05:00 | Zone | 2 | Starting to warm up, Hr going u... | 🔊 |
| 07:00 | Prompt | | Starting to feeling good, ½ wa... | 🔊 |
| 10:00 | Prompt | | Almost warmed up, move aroun... | 🔊 |
| 14:30 | Prompt | | Starting first interval in 30 | 🔊 |
| 15:00 | Zone | 3 | Start of 1 minute interval | 🔊 |
| 15:50 | Info | Heart Rate | | |
| 15:50 | Info | Current Zone | | |
| 15:50 | Info | Target Zone | | |
| 06:00 | Zone | 1 | Begin 2 minute recovery | 🔊 |
| 18:00 | Zone | 3 | Begin 2 minute interval | 🔊 |
| 19:30 | Info | Heart Rate | | |
| 19:30 | Info | Current Zone | | |
| 19:30 | Info | Target Zone | | |
| 00:00 | Zone | 1 | Begin 2 minute recovery | 🔊 |
| 22:00 | Zone | 3 | Begin 3 minute interval | 🔊 |
| 24:30 | Info | Heart Rate | | |
| 24:30 | Info | Current Zone | | |
| 24:30 | Info | Target Zone | | |
| 25:00 | Zone | 1 | Begin 2 minute recovery | 🔊 |
| 27:00 | Zone | 3 | Begin 4 minute interval | 🔊 |

Tabs: General Info / Workout Events / Advanced Settings

Buttons: Play, Skip, Add, Copy, Move, Remove

Columns also include: Review, Response

FIG. 4

PHYSICAL ACTIVITY COACHING PLATFORM WITH DYNAMICALLY CHANGING WORKOUT CONTENT

RELATED APPLICATION

The present application is a continuation of U.S. patent application Ser. No. 15/017,537, entitled, "Physical Activity Coaching Platform with Dynamically Changing Workout Content," filed Feb. 5, 2016 which is a continuation of U.S. patent application Ser. No. 14/251,457, entitled. "Physical Activity Coaching Platform with Dynamically Changing Workout Content," filed Apr. 11, 2014, that in turn claims the benefit of priority to U.S. Pat. App. Ser. No. 61/856,500, entitled "Physical Activity Coaching Platform With Dynamically Changing Content" filed on Jul. 19, 2013, the contents of which are hereby fully incorporated by reference.

TECHNICAL FIELD

The subject matter described herein relates to a computer implemented coaching platform that takes into account contextual data of a user and/or his or her environment while the user is undergoing physical activity in order to provide dynamically changing content.

BACKGROUND

Traditional consumer electronics devices that provide users (athletes) information during physical activities such as exercise include a wrist worn device, such as watch. These devices are limited in the amount and type of information that can be delivered on a small screen size. Also when the user is actively using his/her arms it may not be convenient to stop and look at the screen.

SUMMARY

The current subject matter includes a computer implemented coaching platform that provides contextual coaching feedback to users based on their particular circumstances (e.g., biofeedback, environmental data, historical data from the beginning of the workout or past workouts, etc.) and via selection algorithms to pick audio prompts to be played for the user. Because of multiple circumstance options and a variety of audio prompts, the audio coaching prompts will rarely repeat. Therefore, coaching provided by the computer implemented coaching platform can provide a more authentic, engaging and non-repetitive experience to users.

In one aspect, a method is disclosed that includes defining, by a content authoring tool of a coaching platform, a routine definition comprising segments, wherein each segment includes at least one of a segment parameter, a segment goal and a segment prompt library for assisting a user with performing a routine, the at least one segment parameter including at least one of a duration, a distance, and an intensity defining a routine. The segment goal can include a measurement determining whether the user is successfully performing the routine, and the measurement can include one or more of a heart rate, a pace and an intensity associated with the routine. In addition, the method can include downloading to a device associated with the user, based on a received selection by the user, at least a part of the routine definition. The method can further include analyzing, while the user is performing at least a part of the routine, whether at least one received contextual attribute associated with the user satisfies the measurement, the at least one contextual attribute including a biofeedback data of the user. Additionally, the method can include providing a prompt from the segment prompt library of the routine definition, and the prompt can include an audio prompt. Furthermore, at least one of the defining, downloading, analyzing and providing can be performed by at least one data processor.

In one aspect, a method is disclosed that includes defining, by a content authoring tool of a coaching platform, a routine definition comprising segments, wherein each segment includes at least one of a segment parameter, a segment goal and a segment prompt library for assisting a user with performing a routine. The at least one segment parameter can include at least one of a duration, a distance, and an intensity defining a routine, and the segment goal can include a measurement determining whether the user is successfully performing the routine. The measurement can include one or more of a heart rate, a pace and an intensity associated with the routine. The method can further include recording a prompt and storing the prompt in the segment prompt library, the prompt can include at least one of an instruction and an audible cue that can assist the user in successfully performing the routine. In addition, the method can include allowing the device to download at least a part of the routine definition and, upon the user starting the routine, analyzing whether at least one received contextual attribute associated with the user satisfies the measurement. The at least one contextual attribute can include one or more of a biofeedback data of the user. Additionally, at least one of the defining, recording, and allowing can be performed by at least one data processor.

Non-transitory computer program products (i.e., physically embodied computer program products) are also described that store instructions, which when executed one or more data processors of one or more computing systems, causes at least one data processor to perform operations herein. Similarly, computer systems are also described that may include one or more data processors and memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The subject matter described herein provides many advantages. For example, the current subject matter provides an enhanced user experience by providing seamless feedback that dynamically varies during a workout or other physical activity.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

FIG. 3 is a first view of a coach authoring tool.

FIG. 4 is a second view of the coach authority tool.

Like reference symbols in the various drawings indicate like elements.

DETAILED DESCRIPTION

Figure 1:
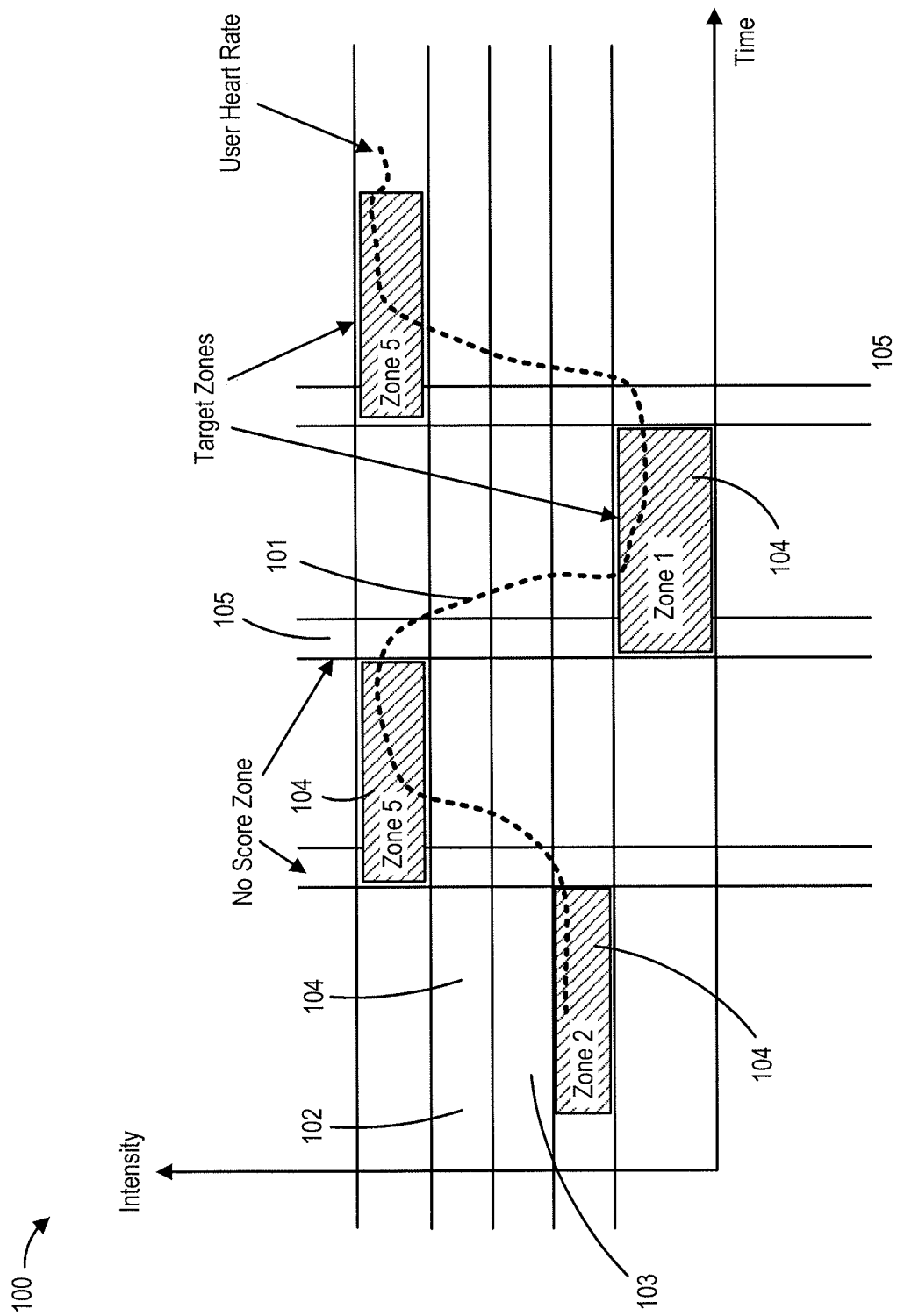
FIG. 1 is a diagram illustrating zones used to construct a workout score.

The current subject matter is directed to rendering specific audio feedback (content player) to a user while he or she is undergoing physical activity, such as exercise workouts. The audio feedback can be provided, for example, in a system such as that described in U.S. patent application Ser. No. 13/720,936, filed on Dec. 19, 2012 and entitled "Fitness and Wellness System with Dynamically Adjusting Guidance", the contents of which are hereby fully incorporated by reference.

A computer implemented coaching platform is described herein that utilizes contextual data associated with a user and/or his environment (e.g., biofeedback data of the user, environmental data associated with the user's location, workout history of the user, etc.) in order to provide dynamically changing content while the user is performing a routine, including physical activity (i.e., performing a workout). The computer implemented coaching platform can include a computer implemented content authoring tool (CAT) that can assist with defining a routine definition or workout definition, which includes a workout parameter and a workout definition prompt library, for assisting (i.e., coaching) a user with performing a workout. The prompt library can include a variety of audio prompts, which can include pre-recorded instructions or cues provided by a coach and can assist the user in performing the workout. On or more prompts of the prompt library can be assigned to segments of the workout or routine, which can be played according to an algorithm that determines which prompts are appropriate to play, such as based on how many times a prompt has been played. The workout parameter can include, for example, one or more of a duration, distance, and intensity associated with the workout.

In addition, the workout definition can include workout definition goals, which can be fitness goals designed for the user to achieve while performing the workout. For example, workout definition goals can define one or more of a heart rate, intensity, calorie expenditure and pace that the user strives to achieve while performing the workout. The computer implemented coaching platform can then analyze collected contextual data associated with the user to determine if the user is achieving workout definition goals. In addition, if the coaching platform determines that the user is not achieving a workout definition goal, the coaching platform can coach the user, such as by playing an audio prompt (e.g., an audio prompt that encourages the user to reach the workout definition goal), in order to assist the user in achieving workout definition goals. Alternatively or in addition, if the computer implemented coaching platform determines that the user is not achieving a workout definition goal, the coaching platform can modify the workout definition, such as lower the intensity associated with a workout definition goal. Furthermore, if the coaching platform determines that the user is achieving a workout definition goal, the computer implemented coaching platform can provide the user with feedback and/or positive reinforcement (e.g., playing an audio prompt that encourages the user to maintain a pace or intensity).

Although some embodiments described herein reference a workout, embodiments of the computer implemented coaching platform, including any features of the computer implemented coaching platform, are not limited to workouts. For example, the computer implemented coaching platform can assist users with performing any number of actions (for example, physical, mental and/or mechanical steps) or routines (e.g., series of actions or steps).

The workout definition can be stored in a computer implemented workout store, which can be accessible by the user. The user can download and/or activate the workout definition in order to complete the workout defined by the workout definition. A virtual coach provided by the computer implemented coaching platform can analyze the user's performance (i.e., analyze collected contextual data associated with the user to determine if the user is achieving workout definition goals) and make dynamic modifications to the workout definition in order to best suit the user's fitness needs and goals. A variety of audio prompts from the prompt library can be provided to the user while attempting to complete the workout, including prompts that are associated with how well the user is completing the workout.

In order to maximize exercise performance, a personal coach can observe a user and give audio feedback, or coaching, to the user. The audio feedback can assist in motivating, encouraging and guiding the user through exercises. Alternatively, a coaching platform or virtual coach, as described herein, can be used instead of a personal coach. The computer implemented coaching platform can provide effective coaching to a user, such as when a personal coach is not available or to supplement personal coaching.

Coaching can include providing specific instructions to a user. The computer implemented coaching platform can provide instructions that dynamically vary based on one or more circumstances or conditions. As used herein, conditions can include a wide range of contextual attributes. For example, the contextual attributes can characterize the user both before and during a workout and/or an environment surrounding a user at least while performing a workout. Other factors can be utilized to generate values for the contextual attributes. Contextual attributes can include, for example, the user's fitness level, recovery level, heart rate, pace, calories burned, overall performance, location, body temperature, environmental temperature, humidity, time of day, distance, time in the workout, and the like. These contextual attributes can be detected by one or more sensors (e.g., cadence sensors, physiological sensors, speedometers, etc.) and mobile devices, such as smart phones, that are coupled to or can characterize the user and/or the local environment. The current coaching platform automates effective coaching by providing a virtual coach that can analyze collected contextual attributes and, for example, compare the collected contextual attribute data with one or more workout definition goals to determine appropriate coaching.

Coaching can also be a reference to the goal of the current workout. The virtual coach provided herein, which can include software and algorithms, can compare the user's performance, including contextual attributes, and execution of the workout to determine if the user is successfully completing, or in-line with, a workout definition, such as a workout definition goal, or not. If the user is not following the workout defined by the workout definition, the virtual coach can prompt and provide coaching (e.g., play an audio prompt, etc.) to correct the user's workout performance. Alternatively or in addition, if the user is successfully completing the workout defined by the workout definition, the virtual coach can play a different prompt to inform the user that he or she is on target.

A workout definition can provide a detailed description of a workout. For example, the workout definition can define the duration, distance and intensities of physical activity at any given time during the workout.

The virtual coach can automatically alter the workout definition, such as when contextual attribute data collected while the user is attempting to perform the workout indicate a need for the workout definition to be altered. For example, the virtual coach can read contextual attribute data characterizing the user's recovery level during the workout and can alter the intensity of the workout definition in order to make the workout more effective to the user. Furthermore, the virtual coach can be multi-dimensional such that it can concurrently compare several different contextual attributes to workout definition attributes at the same time and can make alterations to the workout definition based off of such comparisons, as necessary.

The virtual coach can adjust the workout definition, for example, by reducing the duration (e.g., 60 minutes to 45 minutes) or distance (e.g., 10 miles to 5 miles) of the workout, or lower the intensity of the workout (e.g., instead of running intervals hard at zone five, the target zone can be reduced to zone three). In addition, if a training plan has been configured, as will be described in greater detail below, the virtual coach can choose alternate workouts than what is defined in the training plan.

The virtual coach provided by the computer implemented coaching platform can determine the user's recovery level or readiness to train from, for example, heart rate (HR) readings before and/or during the workout. The user's heart rate variability (HRV) can be used as an index to determine stress levels and readiness to train. In addition to HR values to determine readiness/recovery levels to train, the virtual coach can compare the user's workout history with the user's current performance. For example, the virtual coach can determine whether the user's HR is much higher/lower at a certain pace compared to similar workouts previously performed. Additionally, bio-feedback data (i.e. body temperature, blood pressure, etc.) can be analyzed by the virtual coach to determine one or more conditions of the user.

The virtual coach can also consider a workout score that is calculated based on how well the user is successfully completing a workout (e.g., the user is not able to hit target zones, thus resulting a low score) when determining appropriate alterations to the workout. Environmental factors can also be considered by the virtual coach, such as air temperature, humidity, etc. All these contextual attributes can be monitored by the virtual coach, which the virtual coach can use to consider when determining whether the current workout definition, or workout being performed, is effective for the user. The virtual coach can also consider workout definition goals defined in the workout definition. The virtual coach can read one or more contextual attributes multiple times, such as before and during the workout, in order to analyze and compare their values and adjust the workout definition, as necessary.

In other cases, the virtual coach can dynamically change and adjust the workout definition based on the user's fitness profile (e.g., targeted HR zones, etc.), data input it is receiving (contextual attributes), and/or historical workouts from the user. With such an arrangement, the workout definition can be dynamically changed from what was originally specified, such as by the user.

In another example, the virtual coach can receive contextual attribute data characterizing one or more of the user's heart rate, heart rate variability (HRV), location (e.g., from a global positioning system (GPS) sensor), temperature, pace, distance covered, previous performance during a similar workout, past workout performances, calculations of current training load, etc. Such contextual attributes data can be monitored and analyzed as it is received in order to determine whether any changes should be made to the workout definition.

Coaching can be provided to the user in a variety of ways, including audio prompts (for example, via speakers or headphones worn by the user), which can allow a hands-free way for the user to receive coaching instructions (e.g., increase intensity, slow cadence down, perform exercise, etc.) from the virtual coach. The audio prompts can be obtained from an audio prompt library. In addition, the virtual coaching platform can include algorithms that can determine and select appropriate audio prompts for the workout definition, which can be compiled to create a workout definition prompt library.

For example, the workout definition prompt library can have several audio prompts which can be delivered in response to various contextual attributes detected by the virtual coach. In addition, the virtual coach can keep track of the audio prompts that have been played and pick subsequent prompts to be played that have yet to be played to the user, or have been played the least amount of times, for example, in order to avoid repetitive prompts. The workout definition prompt library can be downloaded or streamed to the user's content player, such as a mobile device (e.g., smart phone), in conjunction with the workout definition, such as via streaming. Alternatively, the workout definition prompt library can be downloaded onto the mobile device for use when needed (i.e., one or more files can be downloaded as opposed to being streamed).

A virtual coach workout engine can be implemented in software that can be downloaded onto a mobile device associated with a user. The workout engine can process the contextual attribute data as it is received and determine whether any modifications should be made to the workout definition.

The virtual coach workout engine can also be implemented as a main loop based on one or more events. For example, the events can be monitored by the virtual coach workout engine as it compares contextual attributes to the workout definition. If the virtual coach workout engine can find a match of contextual attributes in the workout definition, or contextual attributes within a range of the workout definition values, one or more events can be triggered.

The event can be defined as an action to select and play an audio prompt from the workout definition prompt library. Alternatively or in addition, the event can result in a change in display or other type of feedback to user, including physical feedback, such as vibration of a smartphone. The event can also trigger feedback be sent to third parties via e-mail, social networks, and/or messaging protocols to other mobile phones. In addition, the triggers can be based on a variety of contextual attributes (e.g., time, distance, calories, heart rate, etc.). Some contextual attributes can be calculated as an offset from the starting point of the workout.

With reference to diagram 100 of FIG. 1, the virtual coach can calculate a workout score based on how the user is able to follow and achieve workout goals (i.e., target intensities of a workout) defined by the workout definition. For example, if the user is coached to coe at an increased intensity until the user's HR 101 has reached zone four 102, but only gets to zone three 103, the score can be affected. In addition, the user can be asked to run at a certain pace. If the user underperforms and does not run at the requested pace, similarly, the workout score is affected. A workout score can be calculated, for example, by time spent in target intensity zones 104 divided by total time. The workout score, or routine score, can be based on one or more of a variety parameters associated with either the workout or the user, such as contextual attributes. For example, the parameters can include duration, intensity, distance, calories, etc.

The workout definition can include one or more no-scoring segments or zones 105 that do not have a workout definition goal (e.g., an intensity level goal) associated with the segments, and which do not affect a workout score. The no-scoring segments 105 can allow for transitions during a workout, such as intensity changes in the workout (as defined by the workout definition), lags in the user's physiology and HR measurements (such as when the user transitions from one intensity zone to another). For example, a segment in the workout definition can allow for the user's HR to catch up to a higher intensity level and thus not calculate a score (i.e., the workout score is not affected).

The workout definition prompt library can have several prompts for the same contextual attributes and the virtual coach can pick and play one or several prompts at any given time, or when events are triggered. A virtual coach algorithm can choose the audio prompt and can take into account which audio prompts have been played to the user in the past. Therefore, the virtual coach can, for example, select an audio prompt that has yet to be played, or has been played the least number of times.

The associated audio prompts can be implemented with uniform resource locator (URL) links to audio files in a database and can be downloaded at the time of downloading the workout definition or anytime while the user is performing the workout. The audio prompts can be played by a media player, content player, or the like.

The prompt library can include advertising prompts. Each advertising prompt can vary based on a variety of advertising criteria, including contextual attributes and non-contextual attributes. Advertising prompts can also vary based on user profiles, location of the user, time of day, historical activities, and the like. The advertising prompts can be added and played before, during or after the workout.

For example, the advertising prompt can include and deliver the following audible information to the user: "this workout is brought to you by Sponsor X." Alternatively or in addition, the advertising prompt can be based on the location of the workout, including the location where the workout ended. For example, an advertising prompt that is location based can include and deliver the following audible information to the user: "well done with your run, time to hydrate! Your nearest juice bar, Sponsor X, is only 0.5 miles away." This can allow customized delivery of advertisements to users based on one or more contextual attributes, such as location.

In addition, the advertising prompt can be based on a number of calories the user has expended. For example, the advertising prompt can provide suggested energy sources for the user to consume (i.e., certain food, drinks, etc.) based on the amount of calories the user has expended. In addition, the advertising prompt can assist the user with consuming calories that do not exceed the number of calories the user has expended by suggesting energy sources having a calorie content not exceeding the amount of calories expended by the user.

A workout definition can include at least one workout parameter, such as duration, distance or intensity. For example, a workout definition can be defined such that the audio prompts are based off of time, as shown in FIG. 3, where at time zero an audio prompt may be provided to indicate to a user to begin a workout. In some embodiments, a workout definition can be defined such that the audio prompts are based off of distance.

Location contextual attributes can include a GPS coordinate (i.e., latitude and longitude) with a radius. The radius can vary in accuracy and can cover a variety of sized areas. In addition, the radius can be user-defined and/or it can vary based on a particular location of a user (e.g., a mountain trail can have a smaller radius than an open field). Also the workout definition location radius can be adjusted by the virtual coach based on user speed. Therefore, the virtual coach provided by the computer implemented coaching platform can use the location contextual attributes to determine the speed the user is going and compare that speed with a workout parameter defining the speed the user must go in order to successfully complete the workout. As such, if the user is not going fast enough, the virtual coach can play an audio prompt to coach the user to increase the user's speed. Alternatively or in addition, the virtual coach can alter the workout definition in order to better suit the user, such as if the user is unable to reach the speed or pace defined in the workout (i.e., a workout definition goal).

The workout definition can also include metadata that describe different parameters of the workout or workout definition. The metadata can include one or more tags that can enable users to search for workouts, such as amongst a larger collection of workouts or workout definitions. Metadata can include a variety of information, including coach identification, activity type, version, partner (i.e., web based application), price, title, detail description of exercises, metabolic equivalent (MET) values, and links to other materials (i.e., links to videos, etc.). A workout definition can also link with other workouts, such as in order to create a multi-workout scheme or training plan.

For example, a user can search for a workout based on an MET value that has been assigned to the workout (i.e., listed in the metadata of the workout), which can allow a user to search for a workout based on an approximate number of calories the user would like to expend. In addition, the MET values assigned to workouts can be generated, such as based on previous user's profile information and calories expended by users while performing the workouts.

For example, a first user who performs a first workout may expend 1000 calories and this information can be stored by the computer implemented coaching platform. A variety of formulas and devices, including heart rate monitors, can be used to calculate and obtain the number of calories expended during each workout by each user. Additionally, the first user can provide personal information (e.g., body weight), such as from the first user's profile, which can also be stored by the computer implemented coaching platform. This information can be used to calculate an MET value that is specific to the first workout. Additional information, such as an amount of time it took the user to complete the workout or the amount of time the workout defines the workout should take, can also be used in calculating the MET value. Over time, the MET value associated with the first workout can be generated based off of such information collected by a number of users who have completed the workout. In addition, equation 1 can be used to calculate MET values, where time can be the amount of time it took the user to complete the workout or the amount of time the workout defines the workout should take.

$$\text{calories} = (\text{MET value}) \times (\text{user's weight}) \times (\text{time}) \qquad \text{Equation 1:}$$

The following Example 1 shows a part of a workout definition file, which shows an example of a workout parameter (i.e., "TIME"), metadata (i.e., "activity type," "coach_id," etc.) and an audio prompt (i.e., "audio_url": "20d0397ff77ec31df980ecfe3771f561").

Example 1

```
{
    "id": "01bb39e0-bedd-0bf7-1764-f9b0cbc3fa90",
    "coach_id": "5f95d969-04a1-4330-b06a-78c8cb3339 74",
    "author_id": null,
    "activity_type": "RUN",
    "version": "1",
    "title": "RWQS 5.3",
    "description_html": "This run starts with a 5-minute warm-up in zone 1. This is
followed by 30 minutes in zone 2. You will then run five 10-second sprints up a
steep hill.\\Total duration: 39 minutes, 10 seconds",
    "description_short": null,
    "category": null,
    "difficulty": null,
    "audio_url": "1942c4048fa588abb5b5a4035336628f",
    "graph_url": null,
    "icon_url": "n/a",
    "events": [
        {
            "offset": 0,
            "measurement_type": "TIME",
            "type": "zone",
            "options": 1,
            "audio_url": "20d0397ff77ec31df980ecfe3771f561",
            "low_audio_url": null,
            "mid_audio_url": null,
            "high_audio_url": null
        },
        {
            "offset": 60,
            "measurement_type": "TIME",
            "type": "prompt",
            "options": 0,
            "audio_url": "0ec3d35a4f38eab1f40b4eb61c8f3e21",
            "low_audio_url": null,
            "mid_audio_url": null,
            "high_audio_url": null
        }
    ],
    "created_at": "2013-06-24T15:24:34Z",
    "updated_at": "2013-06-24T15:24:34Z",
    "object": "WorkoutHeader",
    "object_md5": "7964e14f74144dfd47e6a61f91e6c88d",
    "last_modified": "2013-06-24T15:24:34Z"
}
```

In some cases, a user may engage in multiple workouts as part of a training plan. A workout or training plan can be characterized by a group of workouts, or workout definitions, that are scheduled by the user throughout the week. Each training plan can define a recommended number of workouts per week.

In some variations, each workout of a training plan can be downloaded individually to a user's mobile device. A training plan can be defined in a JavaScript Object Notation (JSON) format file downloaded from a remote server of the virtual coaching platform. In addition, the training plan workout definition can be adjusted by the virtual coach based on user performance. The training plan can have an array of workout definitions that can be selected by the virtual coach (e.g., the next workout can be selected based on schedule or the users newly determined fitness level).

Example 2 below shows an example of a training plan program, including metadata (i.e., "description_html, "difficulty," etc.):

Example 2

```
{
    "id": "5d200856-78a3-4176-9671-2e2e98dbb20e",
    "author_id": "5f95d969-04a1-4330-b06a-78c8cb333974",
    "partner id": null,
    "type": "DEFAULT",
    "device_type": "IOS",
    "sku": "TEST-1",
    "version": "1",
    "revision": "0",
    "title": "Racing Weight Quick Start",
    "description_html": "This training plan was designed by Racing Weight author Matt Fitzgerald
to help beginner and other low-mileage runners lose excess body fat quickly before starting the
process of training for a big race. The plan is eight weeks long and features six workouts per
week: three runs, two strength workouts, and an indoor cycling workout. Select workouts include
diet and nutrition tips to facilitate fat loss. Coach Matt's Racing Weight Quick Start Guide makes
``` the perfect companion to this training plan.",
 "description_short": "8 weeks, 48 workouts",
 "total_weeks": 8,
 "per_week": 6,
 "difficulty": 5,
 "coach_notes": [ ],
 "icon_url": "e21f69073c954069bdfecffab0facb9f",
 "audio_url": "https://s3.amazonaws.com/mobi.pearsports.public/_608b9913d6c0b7b0f30d662414b2e503.mp3"
,
 "video_url": "",
 "tags ": [ ],
 "archived_at": null,
 "created_at": "2013-06-24T15:24:34Z",
 "updated_at": "2013-06-24T15:24:34Z",
 "workouts": [
  {
   "id": "510309ef-81a8-487a-945b-c910104586cd",
   "plan_id": "5d200856-78a3-4176-9671-2e2e98dbb20e",
   "workout_header_id": "832de644-f307-bdcb-886b-8837912e928e",
   "position": 0,
   "title": "RWQS1.1",
   "description_html": "Congratulations on starting your racing weight quick start training plan. You're in for an exciting journey.\\To do this run you will need access to a hill with a moderate gradient that's long enough to run up for 30 seconds at a time. The workout begins with a 10-minute warm-up. You will then run uphill in Zone 5 for 30 seconds. You'll do this twice with a two-minute jogging recovery after each hill repetition. Finally, you'll cool down for 5 minutes.\\Total duration: 25 minutes",
   "description_short": "25 min hill repetitions run",
   "scheduled_at": null,
   "week_day": null,
   "week_num": null,
   "icon_url": "525221a1227c681f67a59e0a6601fef5",
   "audio_url": "https://s3.amazonaws.com/mobi.pearsports.public/_572611b7f2e791b7f7c5dd63cec33eb3.mp3",
   "video_url": "",
   "active": true,
   "created_at": "2013-06-24T15:24:34Z",
   "updated_at": "2013-06-24T15:24:34Z",
   "plan_workout_id": "510309ef-81a8-487a-945b-c910104586cd",
   "last_modified": "2013-06-24T15:24:34Z",
   "object": "PlanWorkout",
   "object_md5": "3a38ead97f21f6d56476145a8ac23778"
  },
  {
   "id": "0594b88d-3365-48bb-99cf-c14e24881025",
   "plan_id": "5d200856-78a3-4176-9671-2e2e98dbb20e",
   "workout_header_id": "8cc691bc-c930-1e0d-f66f-e8cae5e21e5e",
   "position": 1,
   "title": "RWQS 1.2",
   "description_html": "This is a full-body strength workout. It includes 10 exercises. Each exercise is done one time. The full session takes about 15 minutes to complete. A chin-up bar, an aerobic step, a stability ball, and an exercise bench are required. Watch the videos demonstrating correct technique for each of the following exercises before you do the workout.\\Giant Walking Lunge\r\nSide Plank\r\nPush-Up\r\nStep-Up\r\nAlternating Single-Leg Reverse Crunch\r\nChin-Up\r\nSwiss Ball Hamstrings Curl\r\nReverse Plank\r\nInverted Shoulder Press\r\nEccentric Heel Dip\\Total duration: 20 minutes",
   "description_short": "20 min strength circuit",
   "scheduled_at": null,
   "week_day": null,
   "week_num": null,
   "icon_url": "525221a1227c681f67a59e0a6601fef5",
   "audio_url": "https://s3.amazonaws.com/mobi.pearsports.public/_cd5bb925715d4a3/bcb233836ed77093.mp3",
   "video_url": "https://s3.amazonaws.com/mobi.pearsports.public/_27374b55dcb15e1511bd356dlbadc955.m4v"
,
   "active": true,
   "created_at": "2013-06-24T15:24:34Z",
   "updated_at": "2013-06-24T15:24:34Z",
   "plan_workout_id": "0594b88d-3365-48bb-99cf-c14e24881025",
   "last_modified": "2013-06-24T15:24:34Z",
   "object": "PlanWorkout",
   "object_md5": "6c9214de270f4278f084471ee6daf0b8"

```
        }
    ],
    "object": "Plan",
    "object_md5": "cc0763e279e2b864d56eb633ddbb38da",
    "last_modified": "2013-06-24T15:24:34Z"
}
```

The computer implemented coaching platform can include a workout store that can include a variety of workouts (i.e., workout definition with prompt library) which in turn can be stored digitally to a database. The workouts, or workout definitions, can be stored, deployed, accessed, and otherwise manipulated via various application programming interfaces (API's), such as for downloading workouts to a virtual coach workout engine. In addition, the API can provide access to a database that stores information related to the workouts, or workout definitions.

The workout store API can receive information about the user profile, including last workout heart rate log details, user's preferences, gender, workout history, race results, current location, weight, height, favorite sports, past injuries, current fitness level, activity class, etc. When available, all received data and workout downloads, workout ratings, workout results, etc. can be stored in the user profile.

Protection against unauthorized copying of workout definitions to other devices, such as other user's mobile devices that have not paid for the workout definitions (including audio prompts), can be implemented by including a user identification tag or a receipt token associated with the workout definitions (e.g., embedded in the workout definition software programs). The user identification tag or receipt token can allow a user to play or interact with a workout definition the user has paid for. However, a non-paying user who has not paid for the workout definition would not be able to match the user identification or receipt token with the non-paying user's personal identification, thus preventing the non-paying user from using the workout definition.

Based on a user profile, the workout store can recommend possible subsequent workouts for the user. For example, a user profile can include a user's current location and the workout store can recommend a location based running trail near the user. The user can use a variety of query mechanism to search for workouts the user is looking for, such as workout location near the user. Other queries can include searches for workouts based on the user's fitness level, fitness goals, etc. As discussed above, workout definitions can include metadata that can assist in searching for particular types of workouts.

The workout store can also use user profiling to passively recommend workouts. These recommended workouts can be sent to the user via the content player, email, SMS, in-app notifications, etc. For example, the workout store may consider users with similar user profiles who have completed similar workouts or users that have a similar fitness level to determine recommended workouts for the users. The workout store may analyze all or a portion of a user profile to find matches for workout or training plan recommendations.

The workout store can return different workouts to a user based on different queries. The workout store can include logic that analyzes the user's HRV, fitness level, recovery time and other data, to offer the best possible workouts for maximizing user's fitness development. The workout store can also recommend workouts (i.e. running routes) that are in the user's geographic area. The virtual coach can also create a user profile of the user and query the workout store for recommended workouts.

The workout store API can receive ratings and comments about the workouts. Therefore the workout store can provide results to a request to show, for example, the most popular running workouts (e.g., the top five running workouts). In addition, the workout store can rate and organize workouts based on a variety of variables, such as workout difficulty, workout duration, etc.

The computer implemented workout store can also keep a log of a user's workout performance, frequency, type, duration, etc. In addition, the workout store can rank users based on different criteria (i.e., user performance of workout). The workout store API can provide the user ranking to the user, such as for viewing and comparing with other users.

The workout store can manage the payments or subscription levels of the user in order to access the workout (i.e., the workout store can check that the user's subscription is valid before the workout purchase is complete).

Figure 2:
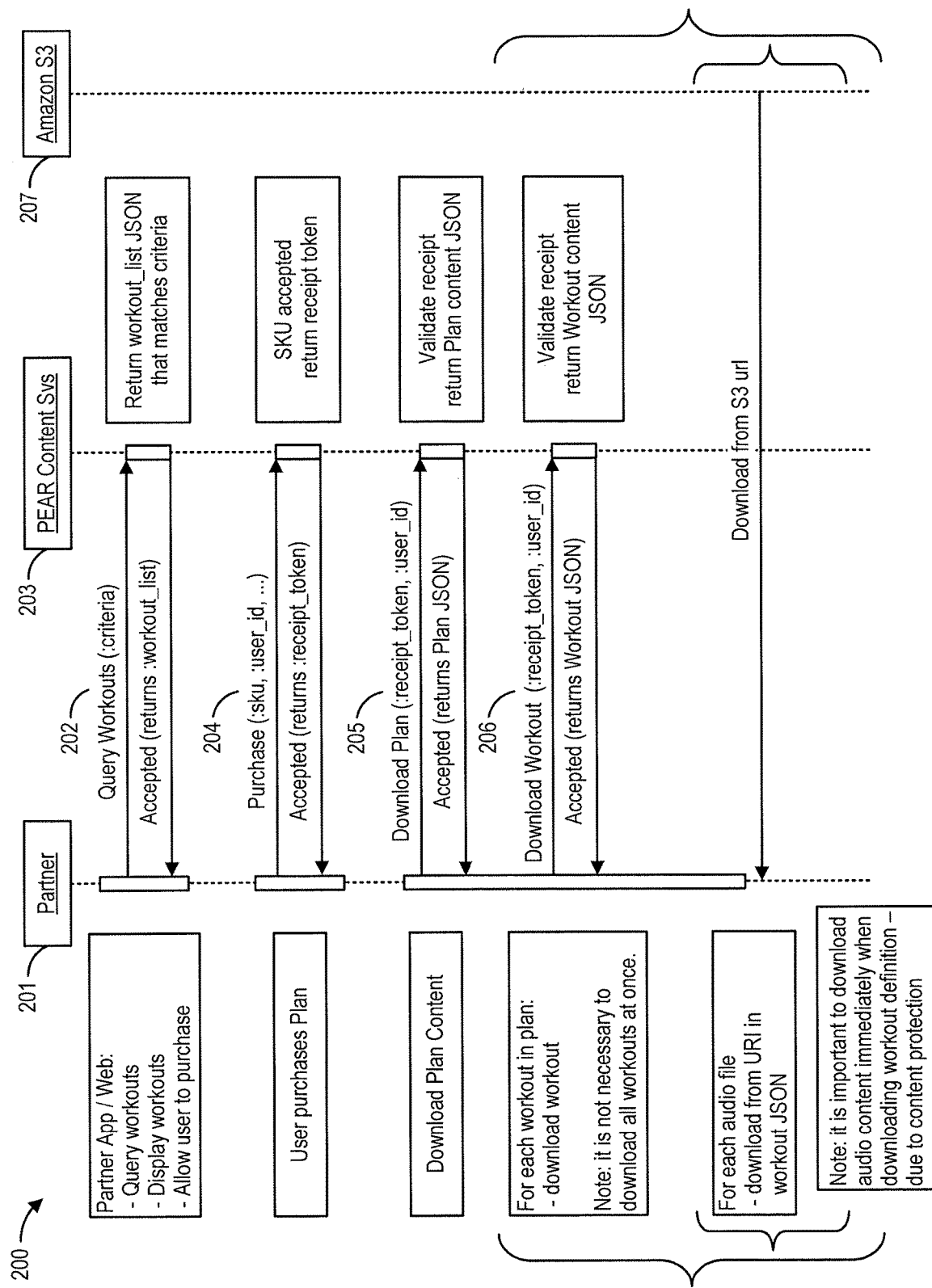
FIG. 2 is a data flow diagram illustrating data exchange among a partner, a coaching platform server, and a clouding computing service provider.

FIG. 2 is a diagram 200 illustrating a data process flow in connection with a computer implemented workout store. The APIs can require authentication and a partner 201, which can be a web based application, can be identified by a user token and secret. APIs can require the user token and secret to be passed to the API. However, basic authentication can also be used in at least some cases.

For example, the APIs can include a query 202. The query 202 can include the user submitting a request to a content server 203 requesting workouts based upon workout characteristics (e.g., author (coach), time duration, distance duration, other metadata tags). In addition, APIs can include a purchase 204. The purchase 204 can allow a user to purchase a workout, such as by using the stock keeping unit (SKU), and download the associated workout definition onto the user's mobile device. Additionally, the APIs can include a download plan 205. The download plan 205 can include information for allowing the user to download the workout plan definition.

For each workout plan selected at least one workout can be downloaded 206 for the user to execute. It may not be necessary to download all of the workouts associated with a workout plan at once. As such, one workout at a time can be downloaded. Audio files can also be downloaded, such as from an online store 307. It can be important to download audio content when downloading a workout definition, such as due to content protection. However, audio content, such as audio prompts, can be downloaded any time after purchase of the workout.

Query plans can include a partner 201 that can render at least a part of the workout store by using a query to retrieve workout store contents. The partner 201 can decide how and what to show of the query results to the user. Alternatively, the partner 201 can use workout store structure that is pre-designed and structured and only render the workout store inside the application as hypertext markup language (HTML) content.

The APIs can return results meeting more than one specific criterion. For example, the request can include to provide all workouts that are longer than 45 minutes and coached by a certain coach (e.g., coach Matt), as shown in Example 3 below.

Example 3

```
{
    "duration_range_high": 2700, // in seconds
    "coach": ["matt"]
}
```

In addition, the results can be ordered by workout plan title, such as in ascending order. Example 4 illustrates an example of query request and results.

Example 4

```
Request:
Method: GET
Params:
{
    "duration_range_low": 0,         // in seconds
    "duration_range_high": 0,        // in seconds
    "distance_range_low": 0,         // in meters
    "distance_range_high": 0,        // in meters
    "num_weeks_range_low": 0,
    "num_weeks_range_high":0,
    "coach": ["coacha","coach2"]     // array: coach names (logically: any of these coaches)
    "tags": ["run", "marathon"]      // array: tags (logically: has all of these tags)
}
Response (success):
HTTP status code: 200
Body (JSON):
{
    [
        {
            "sku": "",              // string, sku used to purchase
            "title": "",            // title
            "description_html": "", // safe HTML description
            "icon_url": "",         // URL to icon (PNG)
            "audio_url": "",        // URL to "helper audio" (.MP3)
            "video_url": "",        // URL to "helper audio" (.OGG)
            "coach_name": "",       // string: name of coach
            "distance": 0,          // in meters
            "duration": 0,          // time in seconds
            "total_weeks": 0,
            "num_per_week": 0,
            "price": 0.00,
            "tags": [""],
            "token": ""             //string: utilized during purchase
        }
    ]
}
Notes:
Results are returned ordered by Coach Name (ascending)
Request:
Method: GET
Params:
-none-
Response (success):
HTTP status code: 200
Body (JSON):
{
    ["name", "name2" ]              // array of coach names
}
```

All fields can, in some implementations, be required. For example, the SKU, price and token can be returned as part of the query plan result data, as shown in Example 5.

Example 5

```
Request:
Method: POST
Params:
{
    "sku": "",           // as sent from Plan Query
    "price": 0.00,       // as sent from Plan Query
    "token": "",         // as sent from Plan Query
    "user_id": ""        // unique - non expiring ID to identify user
}
Response (success):
HTTP status code: 200
Body (JSON):
```

```
{
    "receipt_id": "",
    "user_id": "",
    "purchase_date": "2013-07-01T21:32:38Z"          // GMT based
}
```

In some implementations, all fields can be required. For example, the user_id must be the same user_id that was used when purchasing the plan. The plan can be identified by the receipt_id. The user_id and receipt_id can assist in identifying who purchased the workout definition and can prevent unauthorized users (i.e., users who did not pay for the workout definition) from utilizing the workout definition.

Example 6

```
Request:
Method: POST
params:
{
    "receipt_id": "",
    "user_id": ""          // unique - non expiring ID to identify user
}
Response (success):
HTTP status code: 200
body (JSON):
{
    {
    "id": "5d20085678a3417696712e2e98dbb20e",
    "coach": "Matt Fitzgerald",
    "type": "DEFAULT",
    "sku": "TEST-1",
    "version": "1",
    "revision": "0",
    "title": "Racing Weight Quick Start",
    "description_html": "This training plan was designed by Racing Weightauthor Matt ...",
    "description_short": "8 weeks, 48 workouts",
    "total_weeks": 8,
    "per_week": 6,
    "icon_url": "https://xxxx/e21f69073c954069bdfecffab0facb9f.png",
    "audio_url": "https://xxxx/608b9913d6c0b7b060d662414b2e503.mp3",
    "video_url": "",
    "tags": ["running","mattf"],
    "updated_at": "2013-06-24T15:24:34Z",
    "workouts": [
        {
            "id": "510309ef81a8487a945bc910104586cd",
            "position": 0,
            "title": "RWQS 1.1",
            "description_html": "Congratulations on starting ... ",
            "description_short": "25 min hill repetitions run",
            "week_day": null,
            "week_num": null,
            "icon_url": "https://xxxx/45af69073c954069bdfdadfab0facba0.png",
            "audio_url": "https://xxxx/572611b7f2e791b7f7c5dd63cec33eb3.mp3",
            "video_url": "",
            "object": "PlanWorkout",
            "object_md5": "3a38ead97f21f6d56476145a8ac23778"
            "last_modified": "2013-06-24T15:24:34Z",
        }
    ],
    "object": "Plan",
    "object_md5": "cc0763e279e2b864d56eb633ddbb38da",
    "last_modified": "2013-06-24T15:24:34Z"
    }
}
```

The training content of a workout definition can include audible prompts that can be played for the user under various circumstances, such as to prompt the user about a change in exercises. These audible prompts can be retrieved from a prompt library, with each audible prompt having an associated scoring detail that can be created by a software running on a local computer or a cloud based system, which can be referred to herein as a content authoring tool (CAT) of the computer implemented coaching platform.

The CAT can include or otherwise provide a questionnaire that guides a coach to build workouts. This questionnaire can ask one or more of the objectives of the workout, such as duration, distance, warm-up duration, number of intervals, and intensities of each segment. Based on these questions, a workout definition can be constructed.

The workout definition can include workout events, which can include recommended coaching points (i.e., predetermined circumstances) that are most commonly used, or best practices, in a workout (i.e., the virtual coach or audible prompt can let the user know 10 seconds before every interval that a new interval is about to start).

Therefore, a coach can record and save audio prompts into the prompt library in order to allow the virtual coach to play the saved audio prompts during a workout for use as coaching points. The computer implemented CAT can highlight one or more points in the workout and allow the coach to record their prompt. In some cases, machine generated audio prompts can be generated.

The coach can use prompts in the prompt library that he or she has recorded in the past and reuse them in workouts without needing to record the prompt again. The CAT can also include areas for the coach or CAT to enter workout definition metadata and tags, such as to supplement the workout definition information. These can include price of the workout, coach name, time, and links to audios or videos.

The CAT can assemble training plans out of several workout definitions and, for example, set the rules of at least a recommended workout order. The training plan workout definitions can include several alternative workout options for workouts, which can be a dynamic training plan. The training plan can allow the user to select the next workout definition from an array of workout definitions. The next training plan workout definition can be selected by a virtual coach.

CAT tools can be used between the coach and a content publisher, which can be two separate people. The publisher and coach can communicate via the CAT tool. The publisher can review the workout definition and prompt library and leave notes to the coach to modify the workout definition, such as to repair and re-record the workout definition. The coach can then add more workout definition circumstances and record related audio prompts.

The graphical user interface (GUI) can include a graph of the workout timeline and intensities, such as shown, for example, in FIG. 1. In addition, the workout can include a map of the workouts. The map can include a variety of detailed information, including, for example, elevations and terrain conditions. The GUI can also use color codes to show intensities, which can help a user visualize the workout.

The CAT can predict the training effect or load of the training stress to the user or user fitness levels. For example, the CAT can indicate that the workout definition is a hard workout and is too difficult for anyone with fitness level below a defined threshold.

Figure 4:
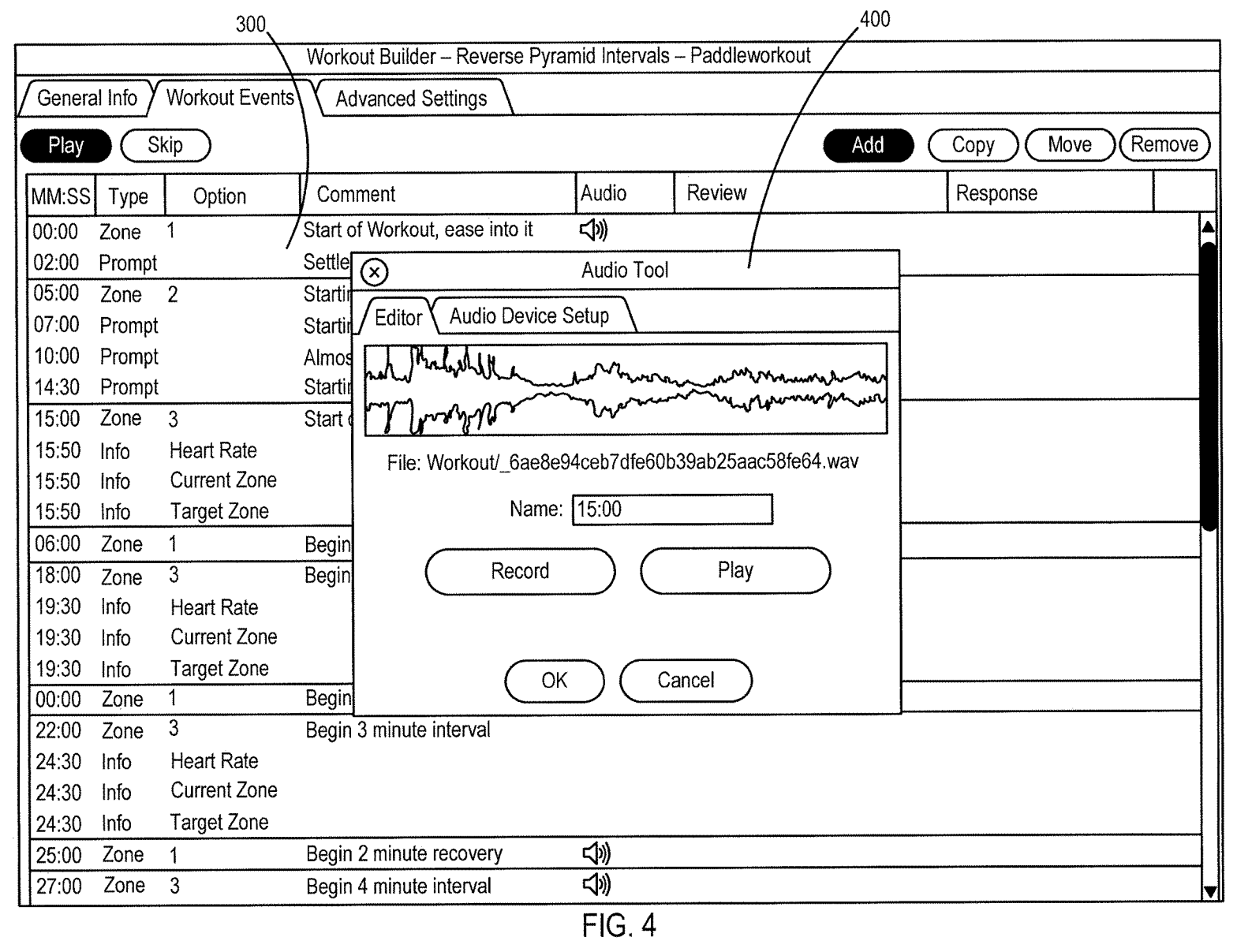

The CAT can automatically adjust the workout scoring formula and no-scoring zones. In addition, the CAT can include a virtual or real athlete video that can enable the coach to associate the coaching for each movement, which can also remind the coach of different prompts to be recorded into the prompt library. The CAT can use system prompts that are pre-recorded. The CAT tool can record live coaching prompts and allow the coach to then assign the live-recorded prompts to the workout timeline, as shown in FIG. 4.

For a multi-dimensional workout, which can include context attributes from several inputs compared simultaneously, the coach can view each dimension independently. For example, the coach can look at the time line of the workout and then choose to add one or more dimensions, such as distance dimensions and calorie dimensions to the multi-dimensional workout.

The CAT can assign advertising prompts to a workout definition or the advertising prompts can be left as open and can be provided to a device associated with a user, such as a mobile device, at the time the workout definition is downloaded or started. Once the workout definition is complete, the CAT tool can enable the coach or publisher to publish the workout on the workout store, or the workout can be embedded or attached into an email and sent digitally, such as directly to a user to be delivered to the virtual coach. Alternatively, the publishing can be done with a direct URL link to the workout. The URL link can expire within certain time frame.

CAT tools can enable the assignment of several simultaneous contextual attributes in the workout definition (i.e., combination and contextual attribute logic—the workout definition could use typical programming logic to create more conditional triggers).

Example logic for conditional triggers can include the following (with contextual attributes defined by "CIR" and prompt library defined by "PL"):

a) if CIRx and CIRy then PL prompt x, or
b) if CIRx and not CIRy, then PL prompt x.
c) If CIR A>x then PL y.

In addition, the virtual coach can keep count of contextual attribute instances (e.g., if CIR A has occurred 10 times, then play PL A10).

FIG. 3 illustrates an example graphical user interface (GUI) of a CAT 300. The CAT can be compiled, for example, by a coach or user intending to build a workout of a workout definition. For example, the coach can first choose a workout parameter 310 (e.g., time, distance, intensity) for the workout definition. As shown in FIG. 3, the coach selected the workout to be time based, which can mean that the workout, or routine, is divided up into time segments 320, with each time segment being assigned at least one of a type of activity 340 (e.g., workout in a certain intensity zone), workout definition goal and audio prompt 350. In addition, one or more time segments can be assigned prompts 360, such as from the prompt library. Additionally, comments 370 can be associated to one or more time segments, such as by the coach compiling the workout definition.

Any number of workout parameters 310 can be used to define a workout definition or workout. For example, the workout can be distance based where the workout is divided into distance segments, with each distance segment, for example, being assigned at least one audio prompt and type of activity. Audio prompts can be assigned to segments of a workout from an audio library, or the coach can record new audio prompts.

FIG. 4 illustrates an example GUI of a CAT 300, including a prompt recording tool 400. The prompt recording tool 400 can allow, for example, a coach to record audio prompts and assign the recorded audio prompts to one or more segments of the workout. For example, the coach can record an audio prompt that informs a user to increase workout intensity. Once the audio prompt is recorded, the coach can either save the audio prompt in an audio prompt library or assign the audio prompt to a segment of the workout, such as a segment where the intensity of the workout is designed to be increased. Any number of audio prompts can be assigned to a segment of the workout, and the virtual coach can choose among the audio prompts assigned based off of, for example, the frequency at which the listed audio prompts have previously been played. The virtual coach can pick audio prompts that either have been played the least or have not been played recently so that the user is not subjected to frequently hearing the same audio prompts.

The coach can use audio prompts in the prompt library that he or she has recorded in the past and reuse them in workouts without needing to record the prompt again. The CAT can also include areas for the coach or CAT to enter workout definition metadata and tags, such as to supplement the workout definition information. These can include price of the workout, coach name, time, and links to audios or videos.

Figure 5:
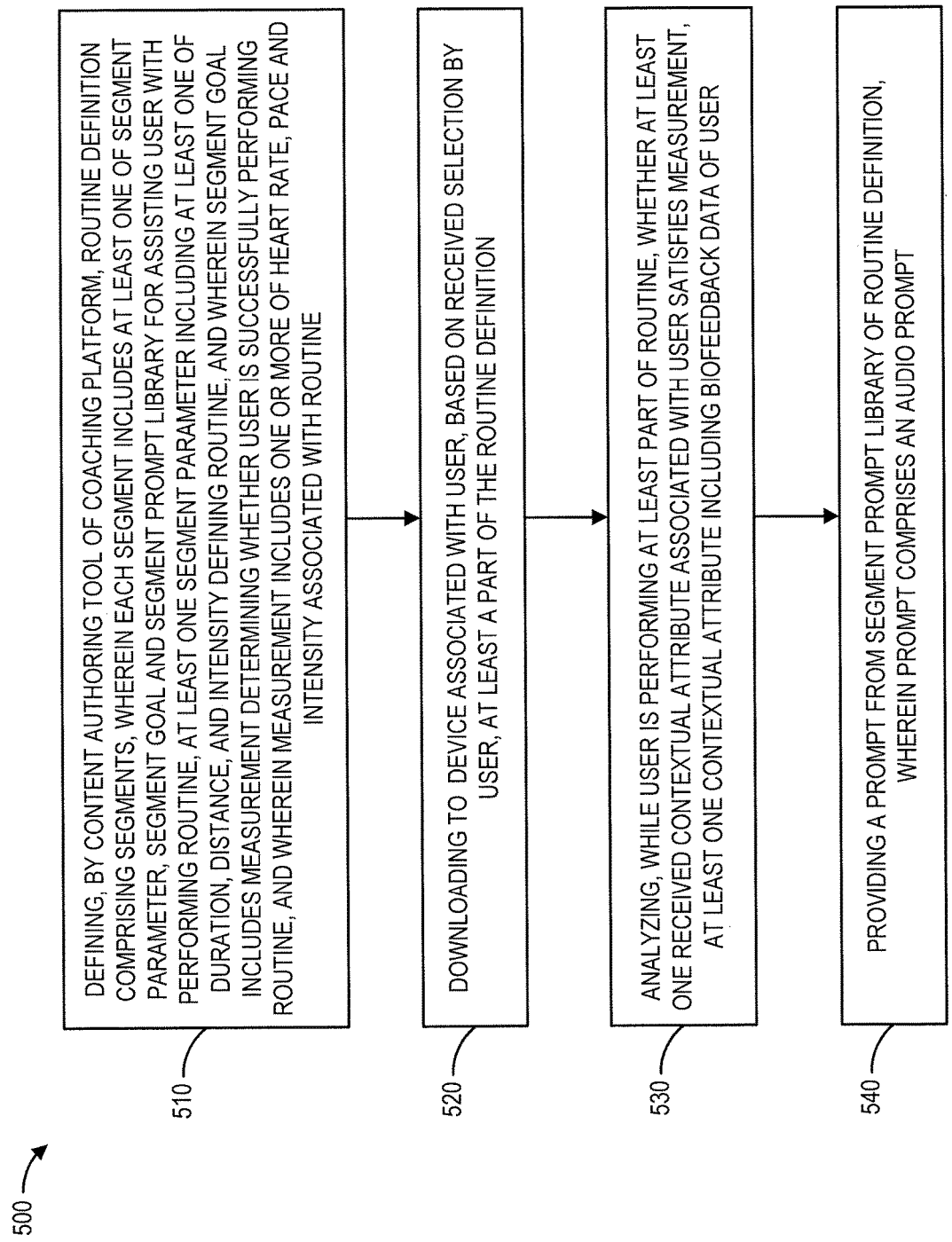
FIG. 5 is a data flow diagram showing at least a part of a method associated with the coaching platform described herein.

FIG. 5 illustrates a data flow diagram showing at least a part of a method associated with the coaching platform described herein. For example, at 510, the CAT of the coaching platform can define a routine or workout definition. The routine definition can include segments, with each segment including at least one of a segment parameter, a segment goal and a segment prompt library for assisting a user with performing a routine. The at least one segment parameter can include at least one of a duration, a distance, and an intensity defining a routine. The segment goal can include a measurement determining whether the user is successfully performing the routine, and the measurement can include one or more of a heart rate, a pace and an intensity associated with the routine. At 520, based on a received selection by the user, at least a part of the routine definition can be downloaded to a device associated with the user. At 530, while the user is performing at least a part of the workout, analysis as to whether a received context attribute associated with the user satisfies the measurement. The contextual attribute can include a biofeedback data of the user. At 540, a prompt from a segment prompt library of the routine definition can be provided. The prompt can be an audio prompt.

One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (sometimes referred to as a computer program product) refers to physically embodied apparatus and/or device, such as for example magnetic discs, optical disks, memory, and Programmable Logic Devices (PLDs), used to provide machine instructions and/or data to a programmable data processor, including a machine-readable medium that receives machine instructions as a machine-readable signal. The term "machine-readable signal" refers to any signal used to provide machine instructions and/or data to a programmable data processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) depicted in the accompanying figures and/or described herein do not necessarily require the particular order shown, or sequential order, to achieve desirable results. Other implementations may be within the scope of the following claims.

What is claimed is:

1. An electronic coaching platform comprising:
an electronic content authoring tool comprising non-transitory machine-readable instructions that are executable on a computer, the content authoring tool being configured to:
    electronically receive a routine definition of a routine of an activity, the routine definition having one or more segments, each segment including at least one of a segment parameter, a segment goal, and a segment prompt library, the segment parameter including at least one of a duration, a distance, and an intensity defining the routine, wherein the segment goal includes a measurement determining whether a user is successfully performing the routine, and wherein the measurement includes one or more of a heart rate, a pace and an intensity associated with the routine,
    retrieve, based on a received selection by the user, at least part of the routine definition to download to an electronic device associated with the user,
    format the routine definition in a non-transitory machine-readable format for electronic transmission via a communications network from the computer,
    store each formatted routine definition in a memory,
    receive biofeedback data from one or more sensors associated with the user and connected with the electronic device, the biofeedback data providing at least one contextual attribute associated with the user while performing the routine to analyze the at least one contextual attribute based on the segment goal of the routine definition to determine a state of the user during each segment of the routine
    calculate, while the user is performing at least a part of the routine, a routine score based on the biofeedback data and based on whether the at least one contextual attribute associated with the user satisfies the measurement, the routine score indicating how the user is able to follow and achieve segment goals defined by the routine definition, and
    adjust the segment parameter, based on the routine score and upon determination that the at least one contextual attribute does not satisfy the measurement and based on historical workouts of the user; and
a workout store in digital communication with the memory of the content authoring tool to receive one or more routine definitions defined by the content authoring tool in the non-transitory machine-readable format, the workout store configured to:
    store the one or more routine definitions and metadata associated with the one or more routine definitions in a database,
    organize the stored one or more routine definitions and metadata for access by a workout engine hosted on the electronic device associated with the user, the workout engine being configured to select one or more prompts from the segment prompt library based on the state of the user or the user's performance of the routine and the routine score, the one or more prompts including sensory feedback information associated with the routine, the sensory feedback information being formatted as a combination of visual feedback, auditory feedback, and tactile feedback.

2. The electronic coaching platform in accordance with claim 1, wherein the workout engine is configured to generate a modified segment parameter based on the state of the user or performance of the routine, and selecting a prompt from the segment prompt library that includes sensory feedback information representing the modified segment parameter.

3. The electronic coaching platform in accordance with claim 2, wherein the modified segment parameter includes an increased or decreased duration, distance or intensity of the routine.

4. The electronic coaching platform in accordance with claim 1, wherein the state of the user includes a performance of the routine as compared to the segment goal.

5. The electronic coaching platform in accordance with claim 1, wherein the at least one contextual attribute characterizes the user both before and during a workout.

6. The electronic coaching platform in accordance with claim 1, wherein the at least one contextual attribute includes at least one of a fitness level, a recovery level, a heart rate, a pace, calories burned, overall performance, a user location, a body temperature, an environmental temperature, a humidity level, a time of day, environmental data associated with the user location, biofeedback data of the user, a workout history of the user, a distance, and a time in the workout.

7. The electronic coaching platform in accordance with claim 1, wherein the content authoring tool enables the coach to define a training plan comprising a plurality of routine definitions.

8. The electronic coaching platform in accordance with claim 1, wherein the organizing of the one or more routine definitions in the workout store is based at least in part by the metadata.

9. A method comprising:
defining, by a content authoring tool of a coaching platform, a routine definition comprising one or more segments, wherein each segment includes at least one of a segment parameter, a segment goal and a segment prompt library for assisting a user with performing a routine, the segment parameter including at least one of a duration, a distance, and an intensity defining a routine, and wherein the segment goal includes a measurement determining whether the user is successfully performing the routine, and wherein the measurement includes one or more of a heart rate, a pace and an intensity associated with the routine;
formatting the routine definition for storage in a workout store, wherein the workout store organizes one or more routine definitions for access by a device associated with the user;
downloading to the device associated with the user, based on a received selection by the user, at least a part of the routine definition;
receiving, by at least one data processor, contextual attributes detected by one or more sensors associated with the device, wherein the contextual attributes comprise biofeedback data of the user and data of a local environment of the user, the data of the local environment indicating at least one of air temperature, humidity, elevation, or terrain conditions;
calculating, while the user is performing the routine, a routine score based on the biofeedback data and based on the data of the local environment indicating the at least one of air temperature, humidity, elevation, or terrain conditions, wherein the routine score indicates an ability of the user to achieve the segment goal in the local environment;

providing a prompt from the segment prompt library of the routine definition based on the routine score, wherein the prompt comprises an audio prompt;

modifying, by the at least one data processor, the segment parameter of the routine definition based on the routine score and in response to a determination that the at least one received contextual attributes does not satisfy the measurement;

wherein at least one of the defining, formatting, downloading, receiving, calculating, providing, and modifying is performed by at least one data processor.

10. The method in accordance with claim 9, wherein modifying the segment parameter comprises increasing or decreasing at least one of the duration, the distance and the intensity defining the routine.

11. The method in accordance with claim 9, further comprising selecting the prompt from the segment library based on a frequency at which the prompt has been played, wherein the prompt further includes visual feedback and tactile feedback.

12. The method in accordance with claim 9, wherein the prompt includes at least one of an instruction and an audible cue that assists the user in successfully performing the routine.

13. The method in accordance with claim 9, further comprising activating a trigger based on at least one of the contextual attributes associated with the user, wherein the trigger comprises an audible advertising prompt that is selected based on one or more of an advertising criteria, the at least one contextual attribute, a user profile, a location of the user, a time of day, and historical activity associated with the user.

14. The method in accordance with claim 9, wherein the calculating further comprises calculating the routine score based on one or more of a duration, an intensity, a distance, and a calorie.

15. The method in accordance with claim 9, wherein the routine definition includes metadata comprising at least one tag defining features associated with the routine definition that allows the device associated with the user to search for the routine definition based on the at least one tag.

16. The method in accordance with claim 9, wherein a training plan is downloaded to the device associated with the user, the training plan comprising a plurality of routine definitions, and wherein the part of the routine definition is received, based on the received selection by the user, from a memory.

17. The method in accordance with claim 9, wherein the contextual attributes further includes at least one of a fitness level, a recovery level, calories burned, overall performance, a workout history of the user, a location, a body temperature, a heart rate, a pace, a time of day, a distance, and a time in the workout.

18. The method in accordance with claim 9, further comprising analyzing whether at least one of the contextual attributes associated with the user satisfies the measurement, wherein the analyzing is performed while the user is performing at least a part of the routine or after completion of the routine.

19. An electronic coaching apparatus for coaching a user of a routine of an activity, the apparatus comprising:

at least one data processor; and at least one memory storing instructions which, when executed by the at least one data processor, result in operations comprising:

defining, a routine definition comprising segments, wherein each segment includes at least one of a segment parameter, a segment goal and a segment prompt library for assisting the user with performing the routine, the at least one segment parameter including at least one of a duration, a distance, and an intensity defining the routine, and wherein the segment goal includes a measurement determining whether the user is successfully performing the routine, and wherein the measurement includes one or more of a heart rate, a pace and an intensity associated with the routine;

formatting the routine definition for storage in a workout store, wherein the workout store organizes one or more routine definitions for access by a device associated with the user;

downloading to the device associated with the user, based on a received selection by the user, at least a part of the routine definition;

receiving, by at least one data processor, contextual attributes detected by one or more sensors associated with the device, wherein the contextual attributes comprise biofeedback data of the user and data of a local environment of the user, the data of the local environment indicating at least one of air temperature, humidity, elevation, or terrain conditions;

calculating, while the user is performing the routine, a routine score based on the biofeedback data and based on the data of the local environment indicating the at least one of air temperature, humidity, elevation, or terrain conditions, wherein the routine score indicates an ability of the user to achieve the segment goal in the local environment;

providing a prompt from the segment prompt library of the routine definition based on the routine score, wherein the prompt comprises at least one of an audio prompt, a visual prompt, and a tactile prompt; and modifying the segment parameter of the routine definition based on the routine score upon determination that the at least one received contextual attributes does not satisfy the measurement and based on historical workouts of the user.

20. The electronic coaching apparatus in accordance with claim 19, wherein the contextual attributes include at least one of a fitness level, a recovery level, calories burned, overall performance, a workout history of the user, a location, a body temperature, a heart rate, a pace, a humidity level, a time of day, a distance, and a time in the workout.

* * * * *